(12) United States Patent
Neriishi et al.

(10) Patent No.: US 6,861,216 B2
(45) Date of Patent: Mar. 1, 2005

(54) DNA DETECTION DEVICE

(75) Inventors: Keiko Neriishi, Kaisei-machi (JP); Yuichi Hosoi, Kaisei-machi (JP); Chiyuki Umemoto, Kaisei-machi (JP); Nobuhiko Ogura, Kaisei-machi (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 77 days.

(21) Appl. No.: 09/749,410

(22) Filed: Dec. 28, 2000

(65) Prior Publication Data

US 2001/0026917 A1 Oct. 4, 2001

(30) Foreign Application Priority Data

Dec. 28, 1999 (JP) ............................................ 11-372977

(51) Int. Cl.[7] .......................... C12Q 1/68; C12P 19/34; H03G 5/00; G08F 15/00; C07H 21/04
(52) U.S. Cl. ................. 435/6; 435/4; 435/5; 536/23.7; 536/24; 536/29; 382/100; 382/128; 382/129; 382/181; 382/305; 382/312; 345/501; 345/502; 345/522; 345/507

(58) Field of Search ................................ 435/4–6, 91.1, 435/91.2, 288; 382/100, 128, 129–133, 181, 305, 312; 345/501, 502, 522, 507; 536/23–29; 378/42, 190

(56) References Cited

U.S. PATENT DOCUMENTS

| | | | | |
|---|---|---|---|---|
| 4,711,955 A | * | 12/1987 | Ward et al. | .................. 536/29 |
| 6,171,794 B1 | * | 1/2001 | Burchard et al. | |
| 6,256,405 B1 | * | 7/2001 | Some et al. | ................ 382/132 |
| 6,271,002 B1 | * | 8/2001 | Linsley et al. | ............ 435/91.1 |

* cited by examiner

*Primary Examiner*—Carla J. Myers
(74) *Attorney, Agent, or Firm*—Burns, Doane, Swecker & Mathis, LLP

(57) ABSTRACT

A process for detecting a complementary DNA fragment is performed utilizing a DNA micro-array, a radiation image storage panel containing a stimulable phosphor, and a spacer sheet having plural openings.

4 Claims, 2 Drawing Sheets

DNA DETECTION DEVICE

FIELD OF THE INVENTION

The present invention relates to a process for detecting a complementary DNA fragment method utilizing a DNA micro-array and a radiation image storage panel.

BACKGROUND OF THE INVENTION

Recently, a DNA micro-array is widely utilized in gene analyzing technology. The DNA micro-array comprises a support (i.e., micro-chip) of an extremely small area (such as approx. 1 $mm^2$ or less) on which a group of nucleotide derivatives or their analogues (probes, e.g., DNA fragments, synthesized oligonucleotides or polynucleotide, PNA) are fixed. On one DNA micro-array, various kinds of nucleotide probes are fixed separately from each other.

In gene analyzing technology, detection of DNA fragments complementary to oligonucleotide probes whose base sequence is already known is very important.

The conventional procedure for detecting DNA fragments complementary to oligonucleotide probes are conducted in the following steps:

bringing single-stranded sample DNA fragments having a specific label (e.g., fluorescent label or radioactive label) in an aqueous solution into contact with a DNA micro-array having at least two defined areas in each of which a group of nucleotide derivatives and analogues thereof are fixed under such condition that a group of nucleotide derivatives and analogues thereof fixed in one area differs from a group of nucleotide derivatives and analogues thereof fixed in another area, so that DNA fragments complementary to a group of nucleotide derivatives and analogues thereof are fixed by hybridization to the area in which the group is fixed;

removing unfixed sample DNA fragments from the DNA micro-array; and detecting the labeled DNA fragments fixed onto the DNA micro-array by hybridization utilizing an appropriate detection procedure.

If a fluorescent label is employed, fluorometry is performed, while a radioactive label is employed, autoradiography is utilized.

The autoradiography utilizing a combination of a radiographic film and a radiographic intensifying screen is favorably employable as the detection procedure. However, since the amount of DNA fragments to be utilized in the detection is extremely small, the autoradiography sometimes shows unsatisfactory sensitivity.

Recently, a radiation image storing and reproducing method utilizing a radiation image storage panel (which is also named "stimulable phosphor sheet" has been widely employed in place of the conventional autoradiography, because the sensitivity provided by the radiation image storage panel is relatively high, as compared with the conventional autoradiographic system.

The use of the autoradiographic procedure utilizing the radiation image storage panel is already known. See Human Molecular Genetics, 1999, Vol. 8, No. 9, 1715–1722.

According to the studies performed by the present inventors, however, the high sensitivity of the radiation image storage panel sometimes shows analytical errors which are caused by the fact that the high sensitive radiation image storage panel absorbs not only the radiation energy emitted by the target DNA fragments (that is, the complementary DNA fragments but also radiation energy emitted by the non-target DNA fragments (that is, non-complementary DNA fragments) which are inadvertently fixed to the DNA micro-array not by hybridization.

SUMMARY OF THE INVENTION

The present invention provides an improved method for detecting complementary DNA fragments utilizing a combination of the conventional DNA micro-array and the conventional radiation image storage panel, which is almost free from noises caused by the inadvertently fixed non-complementary DNA fragments.

The invention resides in a process for detecting a complementary DNA fragment which rises the steps of:

bringing single-strand sample DNA fragments having a radioactive label in a liquid phase into contact with a DNA micro-array having at least two defined areas in each of which a of nucleotide derivatives and analogues thereof are fixed under such condition that a group of nucleotide derivatives and analogues thereof fixed in one area differs from a group of nucleotide derivatives and analogies thereof fixed in another area, so that DNA fragments complementary to a group of nucleotide derivatives and analogues thereof are fixed by hybridization to the area in which the group is fixed;

removing unfixed sample DNA fragments from the DNA micro-array;

keeping the DNA micro-array in contact with a radiation image storage panel containing a stimulable phosphor via a spacer sheet having openings in the areas corresponds to the areas on which groups of nucleotide derivatives or analogues thereof are fixed, so that the stimulable phosphor sheet can absorb and store radiation energy of the radioactive label coming from the fixed DNA fragments through the openings;

irradiating the radiation image storage panel with a stimulating light, so that the image storage panel releases a stimulated emission from the area in which the radiation energy is stored;

detecting the stimulated emission photoelectrically to obtain a series of electric signals; and processing the electric signals to locate the area in which the complementary DNA fragments are fixed.

The spacer sheet is preferably made of non radiation-transmitting material.

In the process of the invention, the radiation image storage panel is irradiated with a stimulating light preferably after it is separated from the DNA micro-array.

The invention also resides in a kit for detecting complementary DNA fragments comprising a DNA micro-array having at least two defined areas in each of which a group of nucleotide derivatives and analogues thereof are fixed under such condition that a group of nucleotide derivatives and analogues thereof fixed in one area differs from a group of nucleotide derivatives and analogues thereof fixed in another area, a radiation image storage panel containing a stimulable phosphor, and a spacer sheet having openings in the areas corresponding to the areas on which groups of nucleotide derivatives or analogues thereof are fixed.

The invention further resides in a composite structure comprising a DNA micro-array having at least two defined areas in each of which a group of nucleotide derivatives and analogues thereof are fixed under such condition that a group of nucleotide derivatives and analogues thereof fixed in one area differs from a group of nucleotide derivatives and analogues thereof fixed in another area, a spacer sheet having openings in the areas corresponding to the areas on which groups of nucleotide derivatives or analogues thereof are fixed, and a radiation image storage panel containing a stimulable phosphor, overlaid in order, the spacer sheet being positioned in relation to the DNA micro-array in such condition that the openings of the spacer sheet face the areas of the micro-array in which groups of nucleotide derivatives and analogues thereof are fixed.

DETAILED DESCRIPTION OF THE INVENTION

Figure 1:
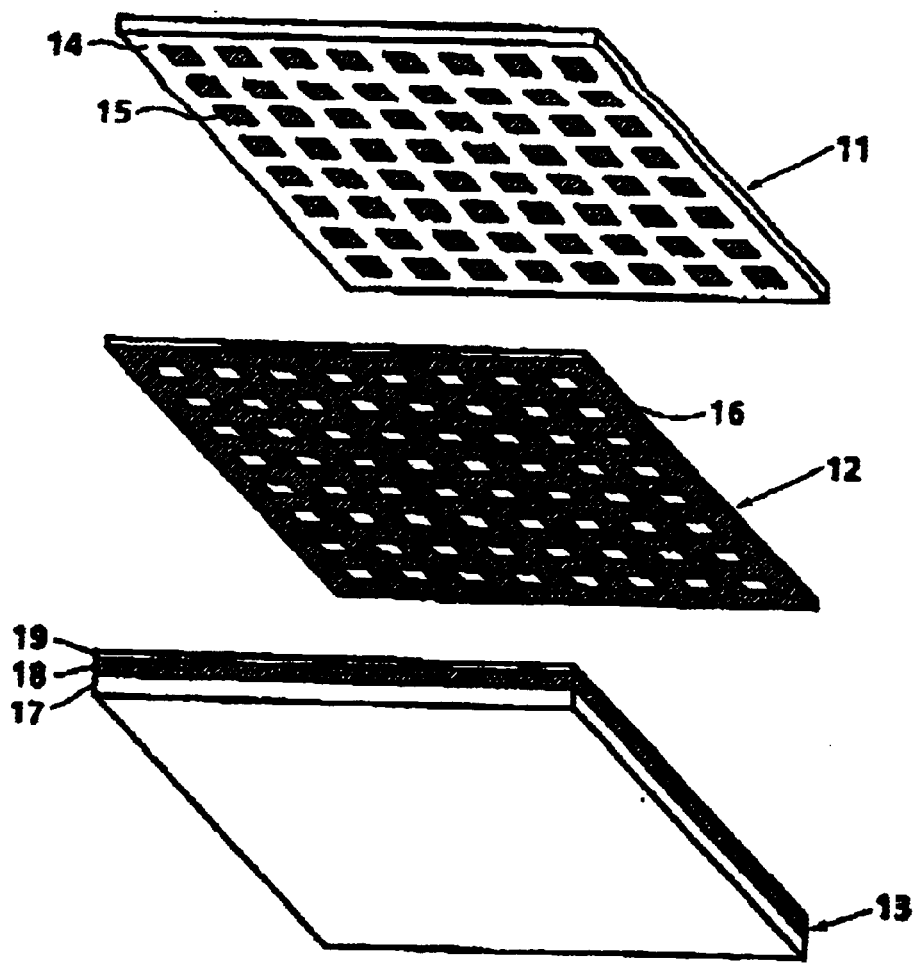
FIG. 1 illustrates a composite structure composed of a DNA micro-array, a spacer, and a radiation image storage panel according the invention under the separated condition.
Figure 2:
FIG. 2 illustrates a composite structure composed of a DNA micro-array, a spacer sheet, and a radiation image storage panel overlaid in order, for subjecting it to autoradiography.

As is shown in FIG. 1 and FIG. 2, the process of the invention utilizes a DNA micro-array 11, a spacer sheet 12 and a radiation image storage panel 13.

The DNA micro-array 11 is composed of a support 14 and many micro-chips 15 arranged on the support. On each micro-chip 15 are fixed a group of probe compounds such as oligonucleotides. Generally, a group of oligonucleotides fixed in one micro-chip have the essentially same base sequence.

The spacer sheet 12 has openings 16 in the positions corresponding to the micro-chips 15 of the DNA micro-array 11, so as not to disturb transmission of radiation energy from the DNA fragment equipped with a radioactive label. The spacer sheet 12 is preferably made of non or less radiation-transmitting material. Examples of the non or less radiation-transmitting materials include metals such as aluminum, brass and stainless and polymers such as polyethylene terephthalate and polyethylene naphthalate. The spacer sheet preferably has a thickness in the range of 10 to 300 μm.

The opening 16 preferably has a shape and a size corresponding to the micro-chip 15 on which a group of nucleotide probes are fixed. The area other than the openings function to disturb the transmittance or penetration of radiation energy from the area other than the micro-chips 15, and further keep the radiation energy emitted from a micro-chip 15 from diffusing to a circumferential area, in other words, distinctly separating a radiation energy transmitted through one opening from a radiation energy transmitted through an adjacent opening.

The radiation image storage panel 13 is composed of a support sheet 17, a stimulable phosphor layer 18, and a protective layer 19.

The stimulable phosphor layer generally comprises a stimulable phosphor in the form of particles and a binder resin.

A number of stimulable phosphors are already know and most of which are employable for the invention. Preferred are an alkaline earth metal halide activated by europium or cerium such as BaFBr:Eu and BaF(Br,I):Eu. A cerium activated rare earth oxyhalide phosphor is also preferred.

The stimulable phosphor layer can be formed on a support sheet by a known method.

The support sheet can preferably is a transparent or light-reflecting plastic material sheet or film. Examples of the plastic materials include polyethylene terephthalate, polyethylene naphthalate, polyamide, polyimide, and aramid resin. The thickness of the support sheet generally is in the range of 50 to 1,000 μm.

The stimulable phosphor layer can be formed, for example, in the following manner which is as such known.

First, the stimulable phosphor particles and a binder are placed in a solvent, and mixed well to prepare a coating liquid in which the phosphor particles are uniformly dispersed in a binder solution. As the binder, various resin materials are known and optionally usable for the invention. The ratio between the binder and the phosphor in the liquid depends on the characteristics of the phosphor and the aimed property of the phosphor layer, but generally they are employed at a ratio of 1:1 to 1:100 (binder:phosphor, by weight). The coating liquid may further contain various additives such as a dispersing agent (for promoting dispersing of the phosphor particles), a plasticizer (for improving binding between the phosphor particles and the binder), an anti-yellowing agent (for inhibiting yellowing of the phosphor layer), a hardening agent and a crosslinking agent.

The coating liquid thus prepared is evenly coated on a short (e.g., glass plate, metal plate, plastic sheet) by known coating means (such as doctor blade, roll coater, and knife coater), and dried to form a phosphor layer. The phosphor layer is once formed on a temporary sheet and then transferred onto the genuine support.

The stimulable phosphor layer can be a deposited phosphor layer or a sintered phosphor layer.

The process for detecting a complementary DNA fragment according to the invention is described below in more detail.

In the first step, single-stranded sample DNA fragments having a radioactive label is brought into contact with a DNA micro-array having two or more defined areas in each of which a group of probe compounds (nucleotide derivatives or their analogue so as DNA molecules, DNA fragments, synthesized oligonucleotides, synthesized polynucleotides, PNA) are fixed. A group of probe compounds fixed in one area differs from a group of probe compounds fixed in another area, so that DNA fragments complementary to a group of probe compounds are fixed by hybridization to the area in which the group is fixed. The single-stranded sample DNA fragments are generally supplied as a solution or dispersion in an aqueous medium.

Subsequently, unfixed sample DNA fragments are removed from the DNA micro-array, for instance, by washing the surface of the DNA micro-array with an aqueous medium, so as to reduce noises and to improve accuracy of the analysis. The problem resides in the fact that DNA fragments which are not complementary to the probe compounds fixed onto the DNA micro-array are irregularly fixed to the surface of the micro-array, because the space of the DNA micro-array sometimes has a great number of functional groups such as hydroxyl groups and amino groups and the DNA fragments also have various functional groups some of which are able to produce bonding with the functional groups on the micro-array.

The DNA micro-array having the sample DNA fragments on its surface is then subjected to autoradiography utilizing a radiation image storage panel. In the autoradiography, the DNA micro-array is kept in contact with a radiation image storage panel via a spacer sheet. The spacer sheet has openings in the areas corresponding to the areas on which groups of probe compounds are fixed, so that the stimulable phosphor sheet can absorb and store radiation energy of the radioactive label coming from the fixed DNA fragments through the openings. The autoradiography is generally performed at a temperature in the range of 0 to 30° C., for one hour to 120 hours.

Generally, the radiation image storage panel is separated from the DNA micro-array and the spacer sheet.

The radiation image storage panel is then subjected to a know radiation image reproducing procedure. In the procedure, the radiation image storage panel is irradiated with a stimulating light, so that the image storage panel releases a stimulated emission from the area in which the radiation energy is stored. The stimulated emission is detected photoelectrically to obtain a series of electric signals. Finally, the electric signals are processed to locate the area in which the complementary DNA fragments are fixed.

Figure 3:
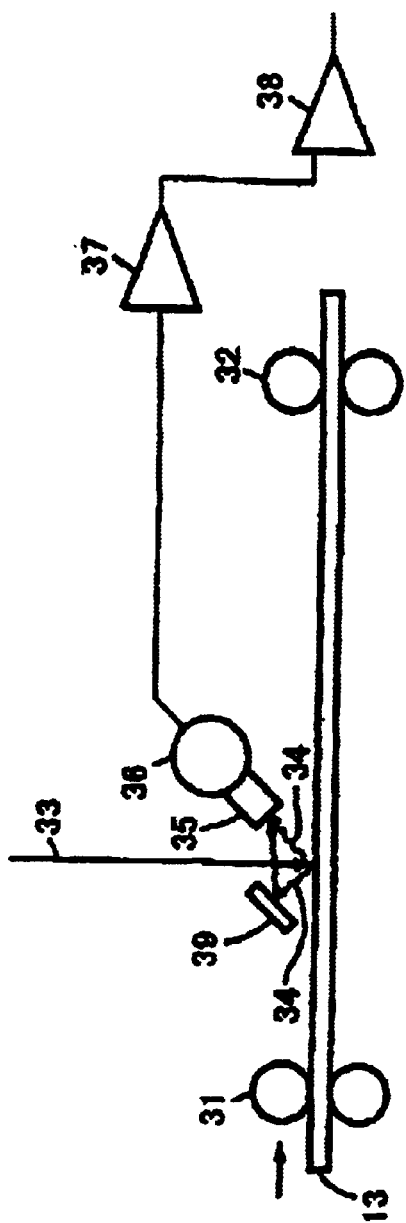
FIG. 3 schematically illustrates a procedure for reproducing a radiation image stored in the radiation image storage panel.

The typical radiation image reproducing procedure is illustrated in FIG. 3.

In FIG. 3, a radiation image storage panel 13 is transferred in the direction of arrow, by means of a pair of rollers 31. On the storage panel 13 is applied a stimulating light 33. A stimulated emission 34 is directly detected by a light detecting means 35 or indirectly detected after reflection on a mirror 39. In the photoelectric conversion means 36, the stimulated emission 34 is converted into a series of electric signals, which are then transmitted to a multiplier 37 and further processed in a processor 38.

What is claimed is:

1. A process for detecting a complementary DNA fragment which comprises the steps of:

bringing a liquid phase comprising single-stranded sample DNA fragments having a radioactive label into contact with a DNA micro-array having a support and at least two defined areas in each of which a group of probe compounds selected from the group consisting of DNA molecules, DNA fragments, synthesized oligonucleotides, synthesized polynucleotides, and PNA (peptide nucleic acid) are fixed under such condition that a group of the probe compounds fixed in one area differs from a group of the probe compounds fixed in another area, so that DNA fragments complementary to a group of the probe compounds are fixed to an area of the micro-array by hybridization of complementary DNA fragments to the probe compounds;

removing unfixed sample DNA fragments from the DNA micro-array;

keeping the DNA micro-array in contact with a radiation image storage panel containing a stimulable phosphor via a spacer sheet intervening between the DNA micro-array and the radiation image storage panel, said spacer sheet being in direct contact with the micro-array and having openings aligned with the ares of the micro-array to which the probe compounds are fixed, so that the radiation image storage panel can absorb and store radiation energy transmitted by the radioactive label of the fixed complementary DNA fragments through the openings in said spacer sheet;

irradiating the radiation image storage panel with a stimulating light, so that the image storage panel releases a stimulated emission from the area in which the radiation energy is stored;

detecting the stimulated emission photoelectrically to obtain a series of electric signals; and processing the electric signals to locate the area in which the complementary DNA fragments are fixed.

2. The process of claim 1, in which the spacer sheet is made of non radiation-transmitting material.

3. The process of claim 1, in which the radiation image storage panel is irradiated with a stimulating light after it is separated from the DNA micro-array.

4. A process for detecting a complementary DNA fragment which comprises the steps of:

bringing a liquid phase comprising single-stranded sample DNA fragments having a radioactive lable into contact with a DNA micro-array having a support and at least two defined areas in each of which a group of probe compounds selected from the group consisting of DNA molecules, DNA fragments, synthesized oligonucleotides, synthesized polynucleotides, and PNA (peptide nucleic acid), are fixed under such conditions that a group of the probe compounds fixed in one area differs from a group of the probe compounds fixed in another area, so that DNA fragments complementary to a group of the probe compounds are fixed to an area of the micro-array by hybridization of complementary DNA fragments to the probe compounds;

removing unfixed sample DNA fragments from the DNA micro-array;

keeping the DNA micro-array in contact with a radiation image storage panel containing a stimulable phosphor via a spacer sheet intervening between the DNA micro-array and the radiation image storage panel, said spacer sheet being in direct contact with the micro-array and having openings aligned with the areas of the micro-array to which the probe compounds are fixed, so that the radiation image storage panel can absorb and store radiation energy transmitted by the radioactive label of the fixed complementary DNA fragments through the openings in said spacer sheet;

irradiating the radiation image storage panel with a stimulating light, so that the image storage panel releases a stimulated emission from the area in which the radiation energy is stored;

detecting the stimulated emission photoelectrically to obtain a series of electric signals; and processing the electric signals to locate the area in which the complementary DNA fragments are fixed, wherein said spacer sheet has a thickness in the range of 10 to 300 µm and is made of a non radiation-transmitting material selected from the group consisting of aluminum, brass, stainless steel, polyethylene terephthalate and polyethylene naphthalate.

* * * * *